United States Patent [19]

Salmond

[11] 3,994,934

[45] Nov. 30, 1976

[54] PROCESS FOR PREPARING $\Delta^{22}$-25-OXY SUBSTITUTED STEROL DERIVATIVES

[75] Inventor: William G. Salmond, Kalamazoo, Mich.

[73] Assignee: The Upjohn Company, Kalamazoo, Mich.

[22] Filed: Jan. 27, 1975

[21] Appl. No.: 544,174

[52] U.S. Cl. .................. 260/397.2; 260/606.5 P
[51] Int. Cl.$^2$............................................. C07J 9/00
[58] Field of Search .................................. 260/397.2

[56] References Cited
UNITED STATES PATENTS 3,822,254  7/1974  Partridge et al. ............... 260/397.2

*Primary Examiner*—Elbert L. Roberts
*Attorney, Agent, or Firm*—Martin B. Barancik

[57] ABSTRACT

A new method of preparing 3α,5α-cyclo-6β-alkoxy-$\Delta^{22}$-25-oxy or acyloxy bisnorcholestane and analogues which involves reacting a bisnorcholanaldehyde with an ylide. Novel cholestanes and i-ethers are also claimed.

12 Claims, No Drawings

PROCESS FOR PREPARING Δ²²-25-OXY SUBSTITUTED STEROL DERIVATIVES

BRIEF DESCRIPTION OF THE INVENTION

A new method for synthesizing 3α,5α-cyclo-6β-alkoxy-25-hydroxy and acyloxy sterol derivatives has been discovered. These sterols are intermediates in the production of 25-hydroxy cholesterol derivatives and thence 25-hydroxy Vitamin D metabolites and their analogues.

This new method comprises stereospecifically reacting an ylide

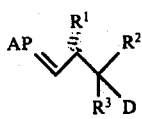

FIG. I wherein A is the portion of a Wittig reagent inert to the reaction medium, and $R^1$, $R^2$ and $R^3$ are each selected from hydrogen and methyl and D is selected from the group consisting of O⁻

and OCR⁴ wherein $R^4$ is selected from the group consisting of alkyl of one to six carbon atoms, phenyl, benzyl, and phenethyl, with 3α,5α-cyclo-6β-alkoxybisnorcholanaldehyde, alkoxy of one to six carbon atoms, inclusive, to form compounds

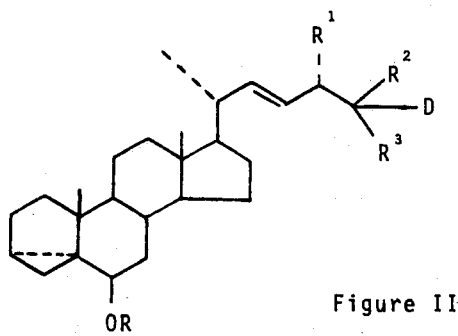

Figure II wherein R is alkyl of one to six carbon atoms, inclusive, and $R^1$, $R^2$, $R^3$ and D are defined as above.

A further aspect of the invention is the preparation of a betaine which comprises reacting the methylene phosphorane

AP=CH₂  FIG. III wherein A is the portion of a Wittig reagent inert to the reaction medium, with the epoxide

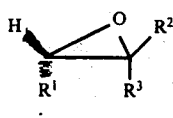

Fig. IV wherein $R^1$, $R^2$ and $R^3$ are each selected from hydrogen and methyl to form

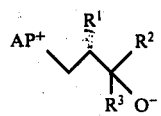

Fig. V

Further aspects of the invention are novel cholestanes and i-ethers.

DETAILED DESCRIPTION OF THE INVENTION

The phrase "alkyl of one to six carbon atoms, inclusive" covers methyl, ethyl, propyl, butyl, pentyl, hexyl and isomers thereof. Examples of isomers are isopropyl, tert.-butyl, neopentyl and 2,3-dimethylbutyl.

The betaine of FIG. V is prepared from the reaction of a methylenephosphorane, FIG. III, with an epoxide of FIG. IV. The A group of the phosphorane is a group commonly employed in a Wittig reagent, see, for example, Tripett, Quart. Rev. XVII, No. 4, p. 406 (1963), and House, "Modern Synthetic Reactions" second edition, p. 682–709. Additionally, the group should be substantially inert with respect to the reaction medium. Examples of such groups include triphenyl, triphenyl substituted with one to three alkyl groups on each phenyl, each alkyl group being the same or different and having from one to four carbon atoms, inclusive. Additionally, A can be a monosubstituted phenyl with two unsubstituted phenyls, for example, (phenyl)₂, p-carboxyphenyl. Other phosphoranes which can be used include the dimethylaminoethylenephosphorane, that is, (Me₂N)₃P=CH₂.

The phosphorane and the epoxide are reacted at room temperature or any convenient temperature of from about 0° to about 40° C. although higher or lower temperature can be employed at times. An inert organic solvent is used as well. See Tripett and House, supra, for suitable solvents. Examples of such solvents include tetrahydrofuran, diethyl ether, hexane, pentane, benzene, heptane, octane, toluene, and dioxane.

Once the betaine is prepared, it is converted to the ylide, FIG. I, by conventional reagents and conditions, for example, by contact with a strong base. Illustrative of the reagents which can be employed to convert to betaine to the ylide are the organo-lithium reagents, such as the alkyl lithium reagents of one to four carbon atoms, sodamide, sodium hydride, lithium amides and so forth. Art-recognized conditions are used for this reaction. The preferred reagent is n-butyl lithium.

The ylide of FIG. I where D is O⁻ is then contacted with the 3α,5α-cyclo-6β-alkoxybisnorcholanaldehyde to form a compound of FIG. II wherein D is O⁻. The temperature at which this reaction occurs is not unduly significant. Temperature of from about 0° to about 40° C. can be employed. The preferred temperature range is from about 15° to about 25° C. It should be noted that the cation is the metal portion of the base employed to convert the betaine to the ylide.

To prepare compounds of FIG. I where D is

the betaine of FIG. V is acylated with the desired $R^4$ acylating agent. For example, an $R^4$ acid anhydride, or and $R^4$ acyl halide, preferably chloride, are readily employed at standard reaction conditions. The resulting salt is then reacted with a strong base such as lithium diisopropylamide to form the ylide of FIG. I (D=acyloxy). This is then reacted with the bisnorcholanaldehyde to form a compound of FIG. II wherein D is

Alternatively, these compounds of FIG. II wherein D is

are prepared by reacting the ylide wherein D is $O^-$ with the bisnorcholanaldehyde and then reacting the resulting 25-oxyanionic steroid with an acylating agent similar to that used earlier, thereby forming the i ether with D as

The above i-ethers can be readily converted to 25-hydroxy-cholesterol and thence to 25-hydroxy-cholecalciferol.

After compounds of FIG. II are prepared, the double bond between $C^{22}$ and $C^{23}$ can be saturated by conventional means thereby preparing the intermediate to 25-hydroxy Vitamin $D_3$ and analogues, see Formula VI.

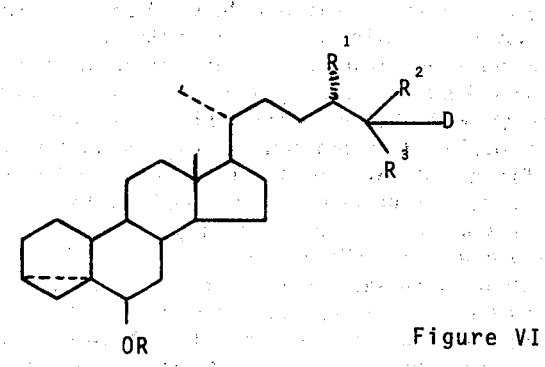

Figure VI $R$, $R^1$, $R^2$, $R^3$, and D defined as above.

A suitable saturation method is catalytic hydrogenation. The hydrogenation is carried out with a noble metal catalyst in a suitable inert organic solvent at appropriate pressures. Platinum or palladium are preferred noble metals. Inert organic solvents such as ethyl acetate, methylene chloride and tetrahydrofuran can be employed. Ethyl acetate is preferred. Any hydrogenation pressure which brings about a reasonable rate of reaction can be used. Pressures as low as 15 psi can be employed. The upper limit of pressure is dependent upon the loss of yield from the opening of the cyclopropane ring. Pressure up to about 100 psi or even higher can be employed with facility.

Following are examples illustrative of the invention scope. These examples are meant to exemplify and not to narrow the invention.

Example 1

$3\alpha,5\alpha$-cyclo-$6\beta$-methoxy-25-hydroxy-26,27-bisnor-cholest-22-ene

Methyltriphenylphosphonium bromide (17.9 g.) is stirred under nitrogen in 150 ml. tetrahydrofuran containing 15 ml. hexamethylphosphoric triamide. n-Butyl lithium (35 ml. of a 1.5M solution in hexane) is added dropwise to yield a bright red solution. This solution is left for 30 minutes before ethylene oxide (ca. 5.0 g.) is added. The reaction vessel is then sealed and the temperature raised to 35° C. for 1 hour. After this time the nitrogen inlet is replaced and the reaction vessel purged with nitrogen to remove the excess ethylene oxide. At this point the reaction mixture is pale yellow. A further 35 ml. of n-butyl lithium is added. This causes a bright red color to be formed, and as the addition continues the temperature rises to 35° C. Fifteen minutes after the addition is completed, a solution of $3\alpha$,-$5\alpha$-cyclo-$6\beta$-methoxybisnorcholanaldehyde (17.0 g. in 150 ml. hexane) is added dropwise until all the color of the ylide is removed. The reaction mixture is then quenched with water and extracted with ethyl acetate. The residue after evaporation and chromatography on neutral alumina gives the desired product as plates recrystallized from acetonitrile, m.p. 104°–105° C.

NMR ($CDCl_3$):
0.3–0.67m; 0.73s (3H); 1.01s (3H); 1.01d, J=6Hz, (3H); 2.77 b.t. (1H); 3.30s (3H); 3.60 t, J-6Hz (2H); 5.37m (2H).
$R_f$: (5% $CH_3OH/CHCl_3$) 0.58

Example 2

$3\alpha,5\alpha$-cyclo-$6\beta$-methoxy-25-hydroxy-26,27-bisnor-cholestane. The $\Delta^{22}$ compound (2.0 g.) obtained from Example 1 is dissolved in 40 ml. methylene chloride. 5% Platinum on carbon catalyst (0.5 g.) is added and the mixture hydrogenated at 90 psi for 2 hours. The catalyst is filtered off and evaporation of the filtrate yields a crystalline residue, recrystallized from acetonitrile by displacement of methylene chloride to give needles, m.p. 128°–129° C.

NMR ($CDCl_3$):
0.3–0.67m; 0.73s (3H); 1.01s (3H); 2.77b.t. (1H); 3.30s (3H); 3.60 t, J=6Hz, (2H). $R_f$: (5% $CH_3OH/CHCl_3$) 0.52

Example 3

$3\alpha,5\alpha$-cyclo-$6\beta$-methoxy-$\Delta^{22}$-25-acetoxy, cholestane

To a stirred suspension of methyltriphenylphosphonium bromide (3.57 g.) in dry tetrahydrofuran (30 ml.) is added at room temperature and under a blanket of nitrogen a solution of n-butyl lithium in hexane (15%, 6.3 ml.). Stirring is continued for 30 minutes and then excess isobutylene oxide added. After 1 hour the flask is purged with a stream of nitrogen to remove the excess oxide and then one molar proportion of acetic anhydride is added. After fifteen minutes a solution of lithium diisopropylamide in hexane, prepared from 6.3 ml. of a 15% solution of n-butyl lithium in hexane and 1.1 g. diisopropylamine in 10 ml. hexane, is added, followed thirty minutes later by a solution of 3.4 g. of the bisnorcholanaldehyde in 25 ml. hexane. After yet a further thirty minutes the mixture is poured into methanol and worked up as in Example 1 to yield the 3α,5α-cyclo-6β-methoxy-25-acetoxy, cholest-22-ene.

Example 4

3α,5α-cyclo-6β-methoxy-25-acetoxycholest-22-ene

To a stirred suspension of methyltriphenylphosphonium bromide (3.57 g.) in dry tetrahydrofuran (30 ml.) is added at room temperature and under a blanket of nitrogen a solution of n-butyl lithium in hexane (15%, 6.3 ml.). Stirring is continued for 30 minutes and then excess of isobutylene oxide is added. After one hour the flask is purged with a stream of nitrogen to remove the excess oxide and then a further 6.3 ml. of the n-butyl lithium solution added. After thirty minutes a solution of bisnorcholanaldehyde in hexane (3.40 g. in 30 ml.) is added. After a further 15 minutes, 1.4 ml. acetic anhydride is added. After yet a further 30 minutes the mixture is poured into methanol, and Skellysolve B (ca 200 ml.) is added followed by ca. 20 ml. water. This causes two layers to form, the lower layer containing predominantly the by-product triphenyl phosphine oxide, and the upper layer containing the desired 25-acetate. Drying of the upper layer followed by evaporation yields a residue of the desired 3α,5α-cyclo-6β-methoxy-25-acetoxycholest-22-ene.
NMR (CDCl₃):
δ0.75s (3H); 1.03s (3H); 1.40s (6H); 1.93s (3H); 2.77m (1H); 3.20s (3H); 5.30m (2H).

Example 5

3α,5α-cyclo-6β-methoxy-25-benzoxycholest-22-ene

In a fashion directly analogous to that described in Example 4 but replacing the acetic anhydride by benzoyl chloride, there is obtained the compound 3α,5α-cyclo-6β-methoxy-25-benzoxy-cholest-22-ene.

The $\Delta^{22E}$ compound has the NMR (CDCl₃): δ0.27–0.70m (3H); 0.70s (3H); 0.97d, J=6Hz, (3H); 1.02s (3H); 1.55s (6H); 2.50-2.67m (1H); 2.77t (1H); 3.30s (3H); 5.20-5.50m (2H); 7.23–7.63m (3H); 7.87–8.17m (2H).

The $\Delta^{22Z}$ compound has the NMR (CDCl₃): δ0.27–0.73m (3H); 0.78s (3H); 0.97d, J=6, (3H); 1.03s (3H); 1.58s (6H); 2.67-2.87m (2H); 3.32s (3H); 5.2–5.47m (2H); 7.2–7.58m (3H); 7.88–8.13m (2H).

Example 6

In an analogous manner to Examples 1 through 5 the following illustrative compounds can be prepared.

| | |
|---|---|
| 1) R¹=H, R²=R³=CH₃ | precursor to the compound claimed in U.S.P. 3,786,062 |
| 2) R¹=R²=R³=CH₃ | precursors to 25-OH-D₂ derivatives |
| 3) R¹=H, R²=R³=CH₃ | precursor to 25-HCC |

Example 7

In a manner similar to Examples 1 through 6, compounds where R is illustratively ethyl, propyl, butyl, pentyl, hexyl, isopropyl, tert.butyl, neopentyl, and 2,3-dimethylbutyl are prepared where R¹, R², and R³ are each hydrogen or methyl.

Example 8

In a similar manner to Examples 1 through 7, compounds where R is propionoxy, tert.butoxy, hexoxy, phenylacetoxy, and 2′ phenylpropionoxy are readily prepared.

I claim:
1. A method for preparing $\Delta^{22}$-25-oxy substituted sterol derivatives which comprises reacting an ylide

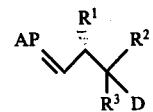

wherein A is the portion of a Wittig reagent of the type AP=CH₂ and is inert to the reaction medium, R¹, R² and R³ are each selected from hydrogen and methyl, and D is O⁻ or

wherein R⁴ is selected from the group consisting of alkyl of one to six carbon atoms, inclusive, phenyl, benzyl and phenethyl with a 3α,5α-cyclo-6β-alkoxybisnorcholanaldehyde wherein alkoxy is from one to six carbon atoms, inclusive, to form compounds of the structure

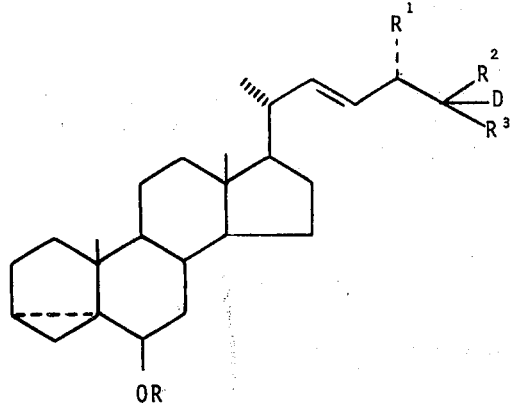

wherein R is alkyl of one to six carbon atoms, inclusive, and R¹, R², R³ and D are as defined above.

2. A method in accordance with claim 1 wherein A is selected from the group consisting of triphenyl, triphenyl substituted with one to three alkyl groups on each phenyl; each alkyl group being the same or different and having from one to four carbon atoms, inclusive, diphenyl p-carboxyphenyl, and trisdialkylamino with alkyl of one to three carbon atoms, inclusive.

3. A method in accordance with claim 1 wherein $R^1$, $R^2$ and $R^3$ are each hydrogen.

4. A method in accordance with claim 1 wherein R is alkyl of one to three carbon atoms, inclusive.

5. A method in accordance with claim 1 wherein $R^1$ is hydrogen and $R^2$ and $R^3$ are methyl.

6. A method in accordance with claim 1 wherein the ylide of claim 1, D being O⁻, is prepared by a. reacting AP=CH₂, said A portion inert to the reaction medium, with the epoxide

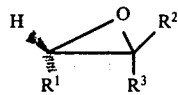

$R^1$, $R^2$ and $R^3$ each selected from hydrogen or methyl to form the betaine

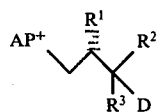

b. converting the betaine of Step a to the corresponding oxyanionic ylide.

7. A method in accordance with claim 6 wherein $R^1$, $R^2$ and $R^3$ are each hydrogen.

8. A method in accordance with claim 6 wherein $R^1$ is hydrogen and $R^2$ and $R^3$ are each methyl.

9. A method in accordance with claim 1 wherein the ylide of claim 1, D being $$\underset{OCR^4,}{\overset{O}{\|}}$$

is prepared by a. reacting AP=CH₂ wherein A is the portion of a Wittig reagent inert to the reaction medium, with the epoxide

 FIG. IV wherein $R^1$, $R^2$ and $R^3$ are each selected from hydrogen or methyl to form compounds of the structure

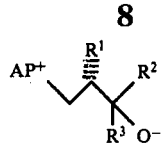 FIG. V wherein D is O⁻ b. acylating D to form salts wherein D is $$\underset{OCR^4,}{\overset{O}{\|}}$$

wherein $R^4$ is selected from the group consisting of alkyl of one to six carbon atoms, inclusive, phenyl, benzyl, and phenethyl, c. converting the salt of Step b to the ylide.

10. A method in accordance with claim 9 wherein $R^1$, $R^2$ and $R^3$ are hydrogen.

11. A method in accordance with claim 9 wherein $R^1$ is hydrogen and $R^2$ and $R^3$ are each methyl.

12. A compound of the formula

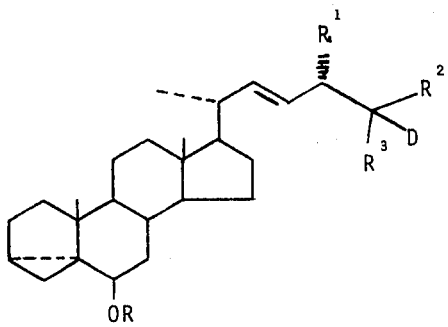

wherein R is alkyl of one to six carbon atoms, inclusive, $R^1$, $R^2$ and $R^3$ are the same or different and are hydrogen or methyl, D is selected from the group consisting of O⁻ and $$\underset{R^4CO}{\overset{O}{\|}}$$

wherein $R^4$ is selected from the group consisting of alkyl of one to six carbon atoms, inclusive, phenyl, benzyl, and phenethyl.

* * * * *